United States Patent
Sauerer et al.

(10) Patent No.: US 12,253,508 B2
(45) Date of Patent: Mar. 18, 2025

(54) METHODS AND SYSTEMS FOR ESTIMATING PROPERTIES OF ORGANIC MATTER IN GEOLOGICAL ROCK FORMATIONS

(71) Applicant: Schlumberger Technology Corporation, Sugar Land, TX (US)

(72) Inventors: Bastian Christoph Eddie Sauerer, Sandsli (NO); Paul Ryan Craddock, Cambridge, TX (US); Wael Abdallah, Dhahran (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 169 days.

(21) Appl. No.: 17/907,409

(22) PCT Filed: Mar. 9, 2021

(86) PCT No.: PCT/US2021/021486
§ 371 (c)(1),
(2) Date: Sep. 27, 2022

(87) PCT Pub. No.: WO2021/216210
PCT Pub. Date: Oct. 28, 2021

(65) Prior Publication Data
US 2023/0118696 A1 Apr. 20, 2023

Related U.S. Application Data

(60) Provisional application No. 63/015,247, filed on Apr. 24, 2020.

(51) Int. Cl.
*G01N 33/24* (2006.01)
*E21B 49/02* (2006.01)
(Continued)

(52) U.S. Cl.
CPC ......... *G01N 33/24* (2013.01); *G01N 21/3563* (2013.01); *G01N 21/65* (2013.01);
(Continued)

(58) Field of Classification Search
CPC .... G01N 33/24; G01N 21/3563; G01N 21/65; G01N 33/241; E21B 49/02; G01J 3/44
(Continued)

(56) References Cited

U.S. PATENT DOCUMENTS 4,714,119 A 12/1987 Hebert et al.
5,667,025 A 9/1997 Haessly et al.
(Continued)

FOREIGN PATENT DOCUMENTS

| CN | 108844941 A | * | 11/2018 | ............. G01N 21/65 |
| WO | WO-2014022757 A1 | * | 2/2014 | ............ E21B 49/005 |
| WO | WO-2015189286 A1 | * | 12/2015 | ............. G01J 3/0202 |

OTHER PUBLICATIONS

Grant A. Myers, Kelsey Kehoe, and Paul Hackley, (2017), "Analysis of Artificially Matured Shales With Confocal Laser Scanning Raman Microscopy: Applications to Organic Matter Characterization," SEG Global Meeting Abstracts : 1683-1698. (Year: 2017).*

(Continued)

*Primary Examiner* — Mohamed K Amara
*Assistant Examiner* — Noah J. Haney
(74) *Attorney, Agent, or Firm* — Jeffrey D. Frantz

(57) ABSTRACT

A method for characterizing organic matter in a geological rock formation includes performing a Raman spectroscopy measurement on a rock sample to acquire a Raman spectrum of the rock sample. The method includes analyzing the Raman spectrum of the rock sample to determine data characterizing at least one Raman spectral feature corresponding to the rock sample, inputting the data characterizing the at least one Raman spectral feature corresponding (Continued)

to the rock sample into a computation model that determines a value of a property of organic matter in the rock sample, and storing or outputting or displaying the value of the property of organic matter in the rock sample. In embodiments, the property of organic material in the rock sample can be a property of kerogen in the rock sample, or a property of asphaltenes or bitumen in the rock sample.

19 Claims, 9 Drawing Sheets

(51) Int. Cl.
    *G01J 3/44*     (2006.01)
    *G01N 21/3563*     (2014.01)
    *G01N 21/65*     (2006.01)

(52) U.S. Cl.
    CPC .......... *G01N 33/241* (2013.01); *E21B 49/02* (2013.01); *G01J 3/44* (2013.01)

(58) Field of Classification Search
    USPC .................................................. 356/301
    See application file for complete search history.

(56) References Cited

U.S. PATENT DOCUMENTS

| | | | |
|---|---|---|---|
| 11,029,250 | B2 | 6/2021 | Sauerer et al. |
| 2009/0260883 | A1 | 10/2009 | Suarez-Rivera et al. |
| 2013/0269933 | A1 | 10/2013 | Pomerantz et al. |
| 2015/0025863 | A1* | 1/2015 | Walls ................ G01N 33/241 703/2 |
| 2015/0090443 | A1* | 4/2015 | Bryndzia ............ G01N 33/241 166/250.01 |
| 2015/0205000 | A1 | 7/2015 | Perkins et al. |
| 2016/0138392 | A1 | 5/2016 | Pomerantz et al. |
| 2016/0146002 | A1 | 5/2016 | Walls et al. |
| 2017/0329045 | A1 | 11/2017 | Myers |
| 2018/0031732 | A1* | 2/2018 | Mosse ................ G01V 20/00 |
| 2019/0025198 | A1* | 1/2019 | Washburn ............ G01N 33/24 |
| 2019/0064039 | A1* | 2/2019 | Ammar ............... G01N 33/241 |
| 2019/0345822 | A1 | 11/2019 | Pfutzner et al. |
| 2020/0064191 | A1* | 2/2020 | Bartholomew ....... G01J 3/4412 |
| 2020/0233114 | A1* | 7/2020 | Sengupta ................ G01V 1/50 |
| 2020/0340352 | A1* | 10/2020 | Guo ..................... G01V 5/12 |

OTHER PUBLICATIONS

Khatibi S, Ostadhassan M, Aghajanpour A. Raman spectroscopy: an analytical tool for evaluating organic matter. J Oil Gas Petrochem Sci. (2018) 2(1): 00007. (Year: 2018).*

Liu D H, Xiao X M, Tian H, et al. Sample maturation calculated using Raman spectroscopic parameters for solid organics: Methodology and geological applications. Chin Sci Bull, 2013, 58: 12851298, doi: 10.1007/s11434-012-5535-y (Year: 2012).*

Cochrane, Corey J., and Jordana Blacksberg. "A fast classification scheme in Raman spectroscopy for the identification of mineral mixtures using a large database with correlated predictors." IEEE Transactions on Geoscience and Remote Sensing 53.8 (2015): 4259-4274. (Year: 2015).*

Wopenka, B., et al. "Murchison presolar carbon grains of different density fractions: A Raman spectroscopic perspective." Geochimica et Cosmochimica Acta 106 (2013): 463-489. (Year: 2013).*

Weck, Philippe F., et al. "Model representations of kerogen structures: An insight from density functional theory calculations and spectroscopic measurements." Scientific reports 7.1 (2017): 7068. (Year: 2017).*

Abdallah, W.A. et al., "Raman Spectrum of Asphaltene.", Energy Fuels 26, 2012, pp. 6888-6896.

Behar, F et al., "Rock-Eval 6 Technology: Performances and Developments", Oil Gas Science and Technology—Reviews I.F.P., 2012, 56(2), pp. 111-134.

Beyssac, O. et al., Characterization of high-pressure, low-temperature metamorphic gradient: a Raman microspectroscopy and HRTEM study. Contributions to Mineralogy and Petrology, 2002, 143, pp. 19-31.

Beyssac, O. et al., "Raman spectra of carbonaceous material in metasediments: a new geothermometer", Journal of Metamorphic Geology 2002, 20, pp. 859-871.

Bonijoly, M. et al., "A Possible Mechanism for Natural Graphite Formation", International Journal of Coal Geology, 1982, 1, pp. 283-312.

Bouhadda, Y. et al., "Characterization of Algerian Hassi-Messaoud asphaltene structure using Raman spectrometry and X-ray diffraction", Fuel 86, 2007, pp. 1855-1864.

Buseck, P. R. et al., "Conversion of carbonaceous material to graphite during metamorphism", Geochimica et Cosmochimica Acta, 1985, 49, pp. 2003-2016.

Cardott, B. J. et al. "Graptolite Reflectance as a Potential Thermal-Maturation Indicator", in Johnson, K.S., ed., Late Cambrian-Ordovician Geology of the Southern Midcontinent, 1989 Symposium, Oklahoma Geological Survey Circular 92, 1991, pp. 203-209.

Cole, G. A., "Graptolite-chitinozoan reflectance and Its Relationship to Other Geochemical Maturity Indicators in the Silurian Qusaiba Shale, Saudi Arabia", Energy Fuels 1994, 8, pp. 1443-1459.

Craddock, P.R. et al., "Thermal Maturity-Adjusted Log Interpretation (TMALI) in Organic Shales", Petrophysics, 2019, 60(5), pp. 540-559.

Diessel, C. F. K., et al., "Coalification and Graphitization in High-Pressure Schists in New Caledonia", Contributions to Mineralogy and Petrology, 1978, 68(1), pp. 63-78.

Goodarzi, F. "Dispersion of optical properties of graphtolite epiderms with increased maturity in early Paleozoic organic rich sediments." Fuel, 1985, 64, pp. 1735-1740.

Goodarzi, F., "Reflected light microscopy of chitinozoan fragments." Marine and Petroleum Geology, 1985, 2(1), pp. 72-78.

Grew, E.S., "Carbonaceous Material in Some Metamorphic Rocks of New England and Other Areas", Journal of Geology, 1974, 82, pp. 50-73.

Jarvie, D. M. et al. "Oil and Shale Gas from Barnett Shale Ft. Worth Basin, Texas", abstract and Slides presented at the AAPG National Convention, 2001, June 3-6, Denver, Colorado, U.S.A., 29 pages.

Kelemen, S. R. et al., "Maturity Trends in Raman Spectra from Kerogen and Coal", Energy Fuels, 2001, 15, pp. 653-658.

Lafargue, E. et al., "Rock-eval 6 Applications in Hydrocarbon Exploration, Production, and Soil Contamination Studies", Revue de L"institut Francais du Petrole, 1998, 53, pp. 421-437.

Landis, C. A., "Graphitization of Dispersed Carbonaceous Material in Metamorphic Rocks", Contributions to Mineralogy and Petrology, 1971, 30(1), pp. 34-45.

Liu, D. et al., "Sample maturation calculated using Raman spectroscopic parameters for solid organics: Methodology and geological applications", China Science Bulletin, 2013, 58(11), pp. 1285-1298.

Marshall, C. P. et al., "Understanding the Application of Raman Spectroscopy to the Detection of Traces of Life", Astrobiology, 2010, 10(2), pp. 229-243.

Nishimura, Y. et al., "Continuous metamorphic gradient documented by graphitization and K-Ar age, southeast Otago, New Zealand", American Mineralogist, 2000, 84, pp. 1625-1636.

Pasteris, J. D. et al., "Raman Spectra of Graphite as Indicators of Degree of Metamorphism", Canadian Mineralogist, 1991, 29(1), pp. 1-9.

Peters, K. E., "Guidelines for Evaluating Petroleum Source Rock Using Programmed Pyrolysis", American Association of Petroleum Geologists Bulletin, 1986, 70, pp. 318-329.

Petersen, H. I. et al., "Reflectance measurements of zooclasts and solid bitumen in Lower Paleozoic shales, southern Scandinavia: Correlation to vitrinite reflectance", International Journal of Coal Geology, 2013, 114, pp. 1-18.

(56) References Cited

OTHER PUBLICATIONS

Potgieter-Vermaak, S. et al., "Raman spectroscopy for the analysis of coal: a review", Journal of Raman Spectroscopy, 2011, 42, pp. 123-129.

Quirico, E. et al., "Maturation grade of coals as revealed by Raman spectroscopy: Progress and problems", Spectrochimica Acta Part A: Molecular and Biomolecular Spectroscopy, 2005, 61, pp. 2368-2377.

Sauerer, B. et al., "Fast and accurate shale maturity determination by Raman spectroscopy measurement with minimal sample preparation", International Journal of Coal Geology, 2017, 173, pp. 150-157.

Schito, A. et al., "Diagenetic thermal evolution of organic matter by Raman spectroscopy", Organic Geochemistry, 2017, 106, pp. 57-67.

Schmidt et al., "Maturity estimation of phytoclasts in strew mounts by micro-Raman spectroscopy", International Journal of Coal Geology, 2017, 173, pp. 1-8.

Schmidt Mumm, et al., "Microscale organic maturity determination of graptolites using Raman spectroscopy", International Journal of Coal Geology, 2016, 162, pp. 96-107.

Schoenherr, J. et al., "Polyphase thermal evolution in the Infra-Cambrian Ara Group (South Oman Salt Basin) as deduced by maturity of solid reservoir bitumen", Organic Geochemistry, 2007, 38, pp. 1293-1318.

Spotl, C., et al., "Kerogen maturation and incipient graphitization of hydrocarbon source rocks in the Arkoma Basin, Oklahoma and Arkansas: a combined petrographic and Raman spectrometric study", Organic Geochemistry, 1998, 28 pp. 535-542.

Tunistra, F. et al., "Raman Spectrum of Graphite", The Journal of Chemical Physics, 1970, 53, pp. 1126-1130.

Wang, G. L. et al., "Determining Resistivity and Low-Frequency Dielectric Constant using Induction Data in the Presence of Strong Induced Polarization", presented at the SPWLA 60th Annual Logging Sympoisum, Jun. 17-19, 2019, The Woodlands, TX, USA, 17 pages.

Wopenka, B. et al., "Structural characterization of kerogens to granulite-facies graphite: Applicability of Raman microprobe spectroscopy", American Mineralogist, 1993, 78, pp. 533-557.

Yui, T.-F. et al., "Raman spectrum of carbonaceous material: a possible metamorphic grade indicator for low-grade metamorphic rocks", Journal of Metamorphic Geology, 1996, 14(2), pp. 115-124.

Search Report and Written Opinion of International Patent Application No. PCT/US2021/021486 dated Jun. 18, 2021, 11 pages.

Schmidt, J. S. et al., "Maturity estimation of phytoclasts in strew mounts by micro-Raman spectroscopy", International Journal of Coal Geology, 2017, 173, pp. 1-8.

\* cited by examiner

METHODS AND SYSTEMS FOR ESTIMATING PROPERTIES OF ORGANIC MATTER IN GEOLOGICAL ROCK FORMATIONS

CROSS-REFERENCE TO RELATED APPLICATION(S)

This application is a U.S. National Stage of PCT Application Number PCT/US2021/021486, filed on Mar. 9, 2021, which subject disclosure claims priority from U.S. Appl. Ser. No. 63/015,247 filed on Apr. 24, 2020, herein incorporated by reference in its entirety.

FIELD

This subject disclosure relates to methods and systems for estimating properties of organic matter in geological rock formations.

BACKGROUND

Raman spectroscopy is an established tool for inspecting carbonaceous materials. In particular, Raman spectroscopy can identify and quantify the presence of carbon bonding environments in carbonaceous materials, including $sp^2$ and $sp^3$ carbons representing carbon atoms bonded in aromatic and aliphatic structures, respectively. In Raman spectra of carbonaceous materials, the vibrational modes of chemical bonds extending from $sp^2$ and $sp^3$ carbons exhibit absorption responsible for the manifestation of the so-called 'G' (graphitic or ordered) and 'D' (disordered) bands. Carbonaceous materials include organic matter, and Raman spectroscopy has been used to study the vibrational modes related to $sp^2$ and $sp^3$ carbons in organic matter components including kerogen, coal, and petroleum asphaltenes. These methods have been established both for bulk formation samples and for organic matter isolated from bulk samples. In this context, kerogen is solid, insoluble, nonvolatile organic matter in sedimentary rock. Kerogen has a high molecular weight relative to bitumen, oil, hydrocarbon gas and/or bitumen forms from kerogen during petroleum generation.

It is known that the Raman spectrum of kerogen and coal, for example, varies as a function of its thermal maturity and its Raman spectrum has been quantitatively correlated to levels of thermal maturation (commonly expressed in units of vitrinite reflectance, % Ro) via one or more Raman spectral characteristics including the so-called 'G' and 'D' band ratios and the 'G' and 'D' band separation as described in PCT Publication No. WO2018/156527. Other methods are known for producing valuable information about the thermal maturity of the kerogen. Such methods include vitrinite reflectance, X-ray diffraction, high-resolution transmission electron microscopy, or dielectric induction. Many of these methods are labor intensive and are performed by an expert, while some are also sample destructive.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

This subject disclosure relates to a method for characterizing organic matter in a geological rock formation. The method includes a) obtaining a rock sample of the geological rock formation; b) performing a Raman spectroscopy measurement on the rock sample to acquire a Raman spectrum of the rock sample; and c) using at least one processor to perform operations that involve i) analyzing the Raman spectrum of the rock sample to determine data characterizing at least one Raman spectral feature corresponding to the rock sample, ii) inputting the at least one Raman spectral feature corresponding to the rock sample into a computation model that determines a value of a property of organic matter in the rock sample given the at least one Raman spectral feature as input, and iii) storing or outputting or displaying the value of the property of organic matter in the rock sample.

In embodiments, the property of organic material in the rock sample is a property of kerogen in the rock sample.

In embodiments, the property of organic material in the rock sample is selected from the group consisting of: density of kerogen, atomic H/C ratio of kerogen, specific surface area of kerogen, macroscopic capture cross-section for thermal neutrons (Sigma) of kerogen, thermal neutron porosity endpoint of kerogen, dielectric permittivity of kerogen, electrical conductivity of kerogen, and a geochemical proxy for kerogen composition such as pyrolysis $T_{max}$ or pyrolysis hydrogen index.

In embodiments, the property of organic material in the rock sample is a property of asphaltenes or bitumen in the rock sample.

In embodiments, the Raman spectroscopy measurement is performed by a Raman spectrometer.

In embodiments, the Raman spectrum of the rock sample comprises spectral intensity for wavelengths that cover the region of the IR spectrum between at least 1000 $cm^{-1}$ and 1877 $cm^{-1}$.

In embodiments, the at least one spectral feature of the rock sample corresponds to one or more Raman bands or modes attributable to organic matter in the rock sample.

In embodiments, the at least one spectral feature of the rock sample is related to particular Raman bands in the rock sample selected from the group consisting of: Raman band positions, Raman band full-width at half-maxima (FWHM), Raman band areas, Raman band amplitudes, ratio of Raman band positions, ratio of Raman band FWHM, ratio of Raman band areas, and ratio of Raman band amplitudes.

In embodiments, the computational model is a linear or non-linear mapping function that relates data characterizing at least one Raman spectral feature of a rock sample to a value of a property of organic matter in the rock sample.

In embodiments, the rock sample is selected from the group consisting of core or plug, rock chips, drill cuttings, or rock outcrop.

In embodiments, the operations of b) are carried out in a laboratory or at a wellsite.

In embodiments, the operations of c) are carried out in a laboratory or at a wellsite.

In embodiments, the operation of a), b) and c) can be repeated for rock samples obtained from different depths of the formation to determine and output a log of an organic matter property of the formation as a function of depth in the formation.

In embodiments, the computation model of c) can be generated by determining data characterizing at least one Raman spectral feature for each one of a plurality of rock samples, and performing correlation and regression analysis on the data characterizing the Raman spectral features corresponding to the plurality of rock samples and data quantifying a known or measured organic property for each one of a plurality of rock samples. The data characterizing at least one Raman spectral feature for each one of the plurality of rock samples can be determined by measuring a Raman spectrum for each one of the plurality of rock samples and analyzing the Raman spectrum for each one of the plurality of rock samples.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

This subject disclosure describes a method that employs a Raman spectroscopy measurement to estimate one or more properties of organic matter (particularly one or more properties of kerogen or asphaltenes) in sedimentary rock where such properties are particularly relevant to oilfield formation evaluation. One example of a kerogen property is kerogen density, which is a necessary input in the determination of density-porosity of kerogen-bearing geological formations, including petroleum source rocks. Another example of a kerogen property is kerogen Sigma (macroscopic cross-section for thermal neutron capture), which is a necessary input in the determination of Sigma-based saturation of kerogen-bearing geological rock formations. An example of an asphaltene property is asphaltene composition that can impact the viscosity and production of heavy oils in petroleum reservoirs. Advantageously, the Raman spectroscopy measurements provide a fast, non-destructive and innovative method for the determination of the desirable organic matter property(ies) performed ideally on bulk formation samples with minimal sample preparation, but are equally applicable to any method for the preparation of the rock samples with organic matter for the Raman spectroscopy measurement.

Figure 1:
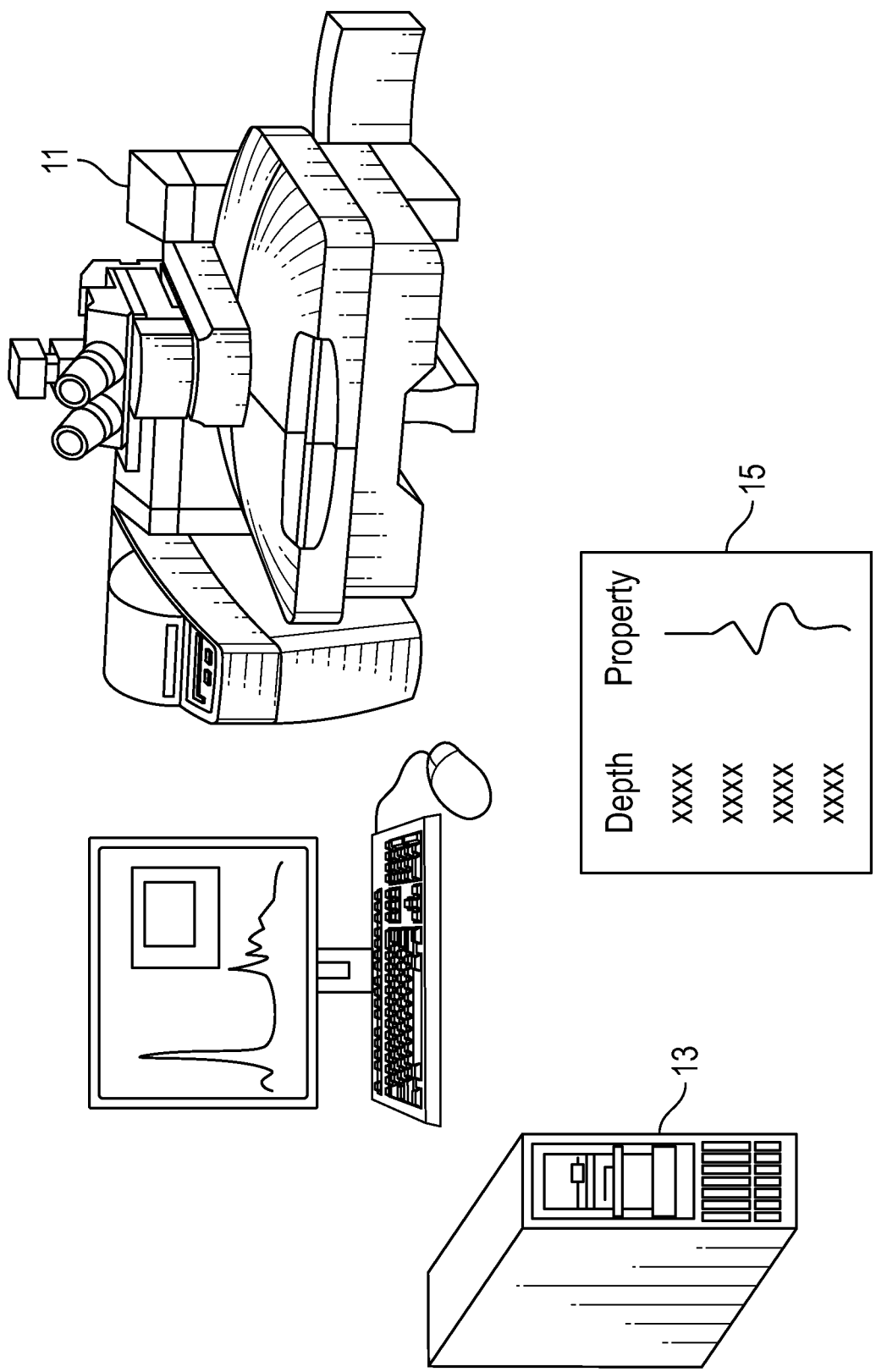
FIG. 1 is a schematic diagram of equipment that performs a Raman spectroscopy measurement on a rock sample of a geological rock formation and analyzes the Raman spectral values obtained from the Raman spectroscopy measurement to determine one or more properties of organic matter (particularly for kerogen or asphaltenes properties) of the rock sample.
Figure 5:
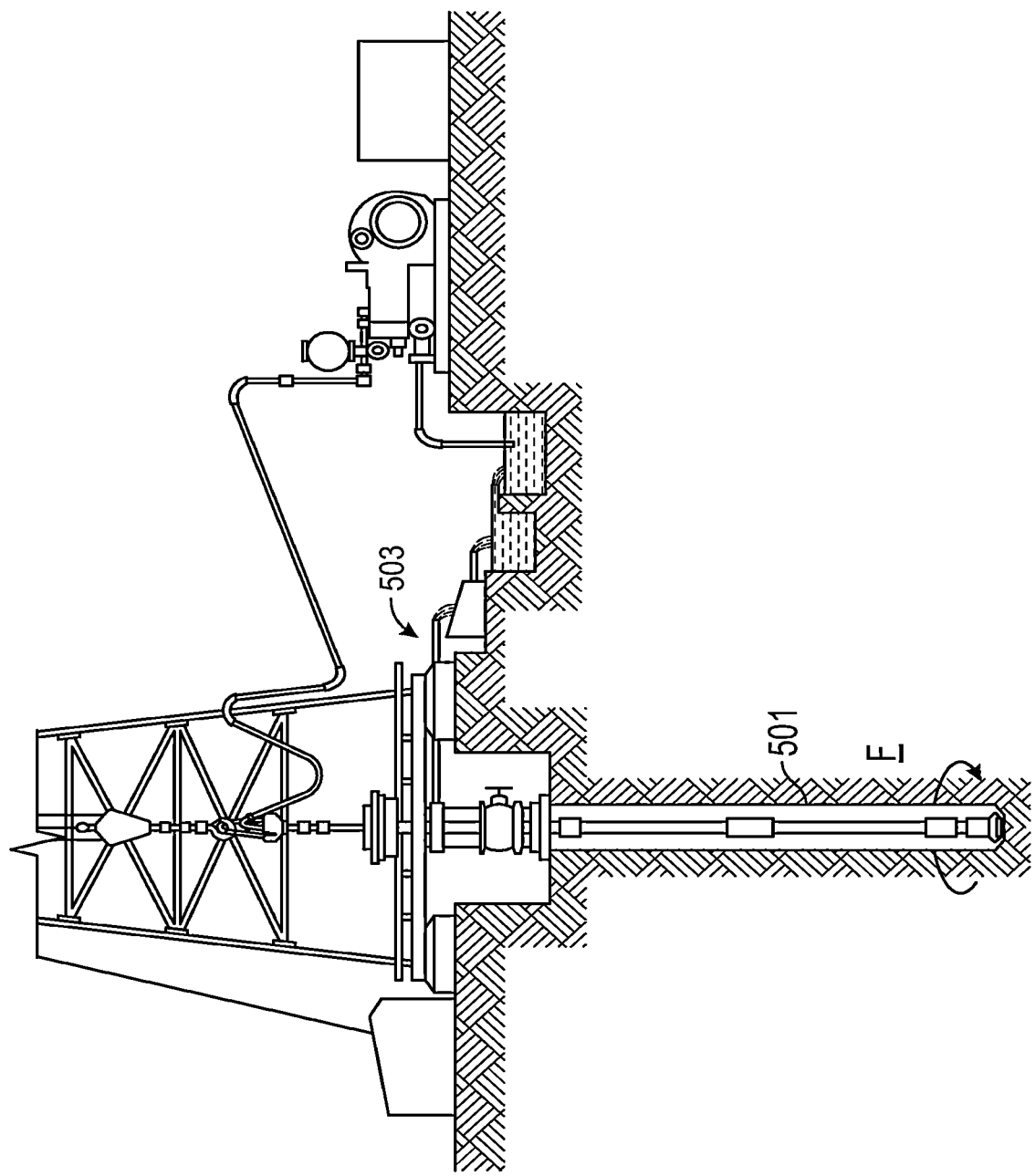
FIG. 5 is a diagram of a wellsite with equipment provided for drilling a wellbore into a geological rock formation and acquiring drilling cutting rock samples of the geological rock formation as the wellbore is drilled.

FIG. 1 illustrates equipment that performs a Raman spectroscopy measurement on a rock sample of a geological rock formation and analyzes the Raman spectral values obtained from the Raman spectroscopy measurement to determine one or more properties of organic matter (particularly for kerogen or asphaltenes properties) of the rock sample. The equipment includes a Raman spectrometer 11 that is configured to perform a Raman spectroscopy measurement on a rock sample of a geological rock formation. The Raman spectroscopy measurement performed by the Raman spectrometer 11 relies on inelastic scattering of photons, known as Raman scattering. Monochromatic electromagnetic radiation from a source interacts with molecular vibrations, phonons or other excitations in the rock sample resulting in a shift in photon energy that gives information about the vibrational modes in the rock sample. The monochromatic electromagnetic radiation is typically from a laser in the visible, near infrared, or near ultraviolet range, although X-rays can also be used. In one embodiment, the Raman spectrometer 11 comprises a Raman microscope such as the Thermo Scientific DXR Raman Microscope sold by Thermo Fisher Scientific, Inc. of Waltham, MA. A computer or processor 13 can be configured to analyze the Raman spectral values obtained from the Raman spectroscopy measurement performed by the Raman spectrometer 11 to determine one or more properties of organic matter (particularly for kerogen or asphaltenes properties) of the rock sample. Such analysis can be performed for rock samples obtained from different depths of the formation to determine and output (e.g., display) a log 15 of the organic matter property (ies) of the formation as a function of depth in the formation. The log 15 may be generated at the wellsite and/or remotely and may be presented as part of a multi-log which presents additional information regarding the geological rock formation and/or drilling process (FIG. 5).

Figure 2:
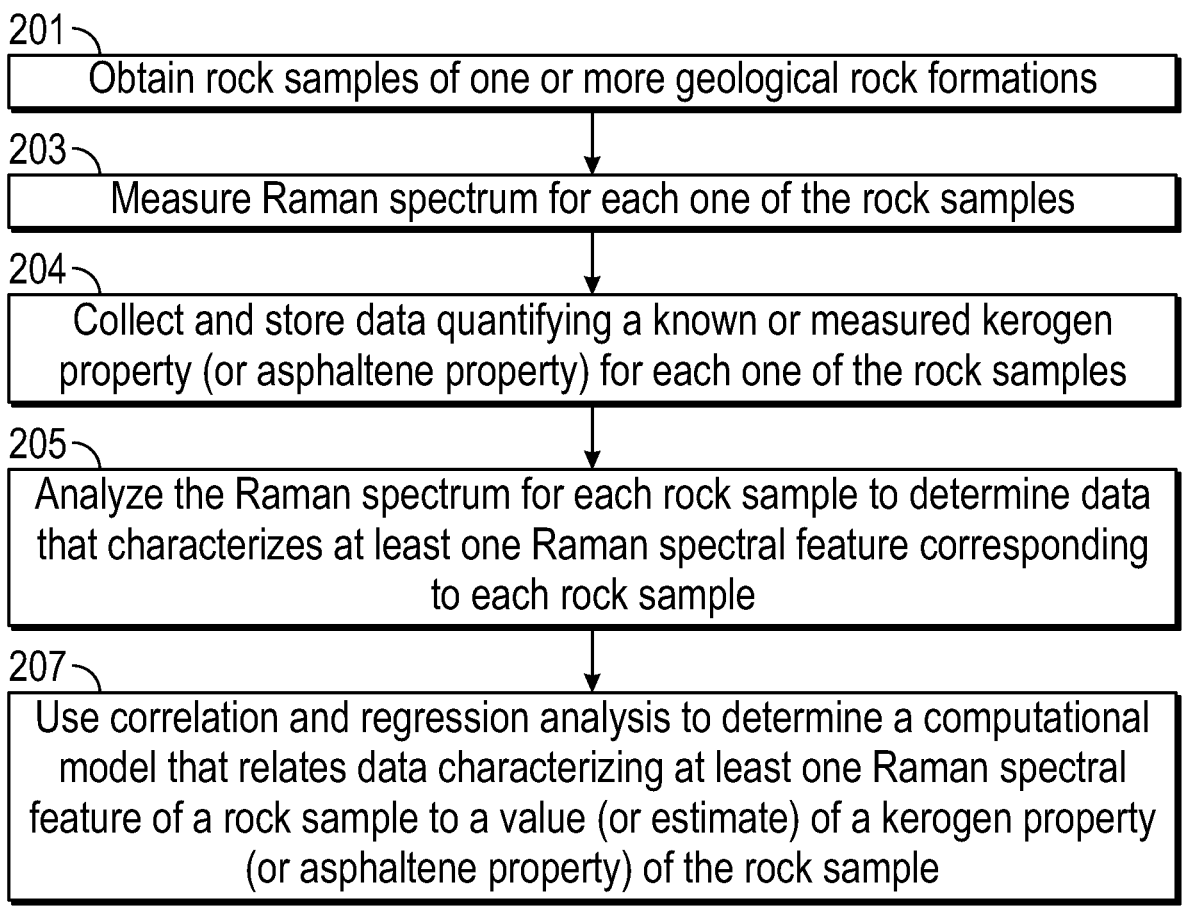
FIG. 2 is a flow diagram of a method that employs Raman spectroscopy measurements on rock samples of one or more geological rock formations and collections of data quantifying a known or measured kerogen property (or asphaltene property) of the rock samples to determine a computation model that relates at least one Raman spectral feature of a rock sample (input) to a value (or estimate) of a kerogen property (or asphaltene property) of the rock sample (output)

FIG. 2 is a flow diagram of a method that employs Raman spectroscopy measurements on rock samples of one or more geological rock formations together with a collection of data that quantifies a known or measured kerogen property (or asphaltene property) of each rock sample to determine a computation model that relates at least one Raman spectral feature of a rock sample (input) to a value (or estimate) of such kerogen property (or asphaltene property) of the rock sample (output).

The method begins in block 201 by obtaining rock samples of one or more geological rock formations. The rock samples can be a plug or sidewall core obtained from a geological rock formation or part thereof (FIG. 4), a drill cutting obtained from a well drilling operation (FIG. 5), rock chips, crushed rock from drill cuttings or a core fragment, outcrop rock, or other suitable rock samples.

In block 203, Raman spectroscopy measurements are performed on the rock samples obtained in block 201 to acquire a Raman spectrum for each one of the rock samples. In embodiments, Raman spectroscopy measurements are performed using one or more Raman spectrometers. In embodiments, the Raman spectrum acquired for each rock sample includes spectral intensity values for wavelengths that cover the region of the IR spectrum between at least 1000 $cm^{-1}$ and 1877 $cm^{-1}$. In embodiments, the Raman spectrum for a given rock sample can be acquired by multiple scans of the given rock sample and averaging the measured Raman spectral response for the multiple scans.

In block 204, data is collected that quantifies a known or measured kerogen property (or asphaltene property) for each rock sample obtained in block 201. The data can be collected from the results of sample analysis that provide relatively accurate measurements of the relevant kerogen property (or asphaltene property) for each rock sample as deemed suitable for the method.

Figure 6:
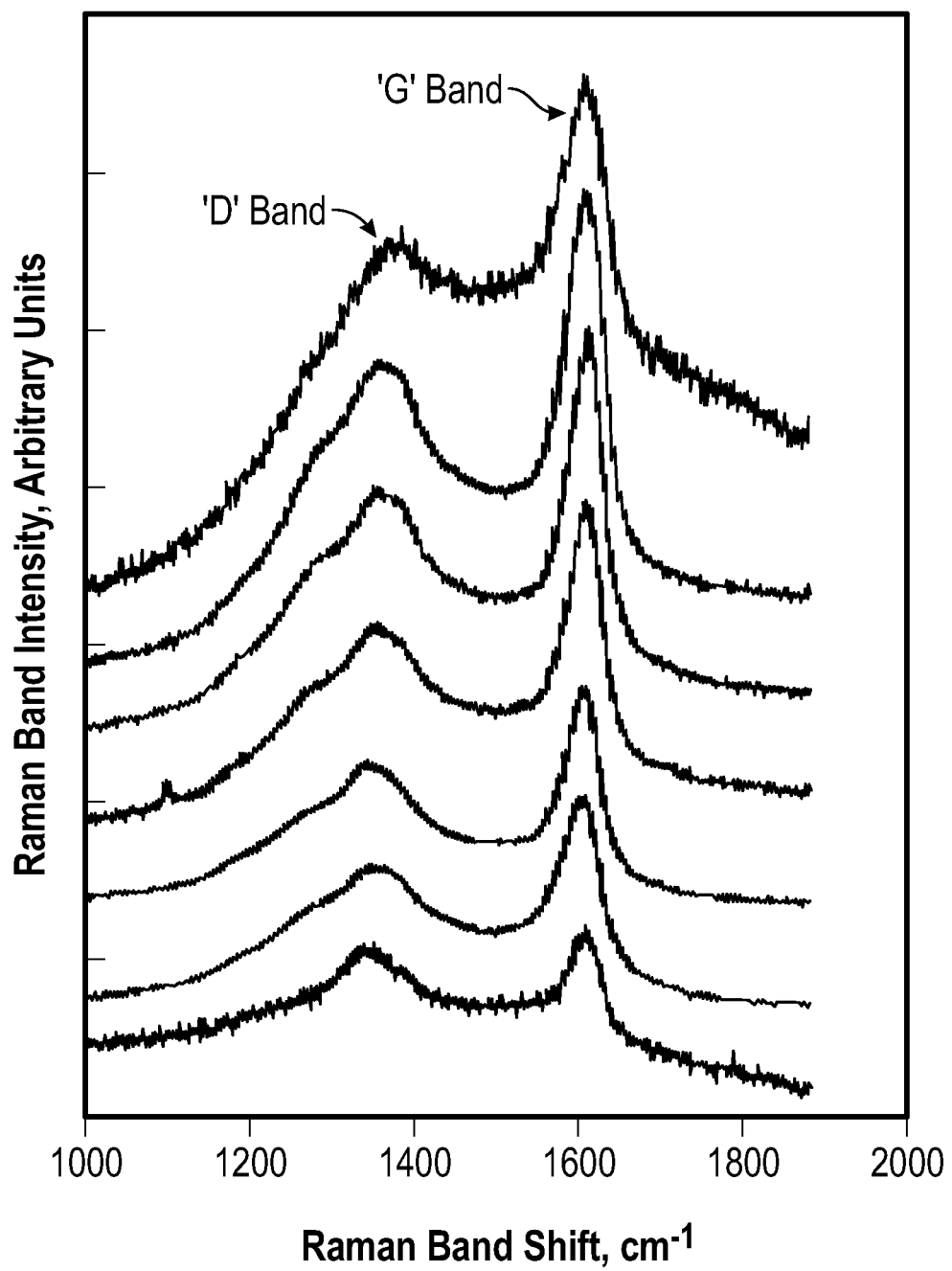
FIG. 6 depicts plots of Raman spectra of organic matter in geological rock formations.
Figure 7:
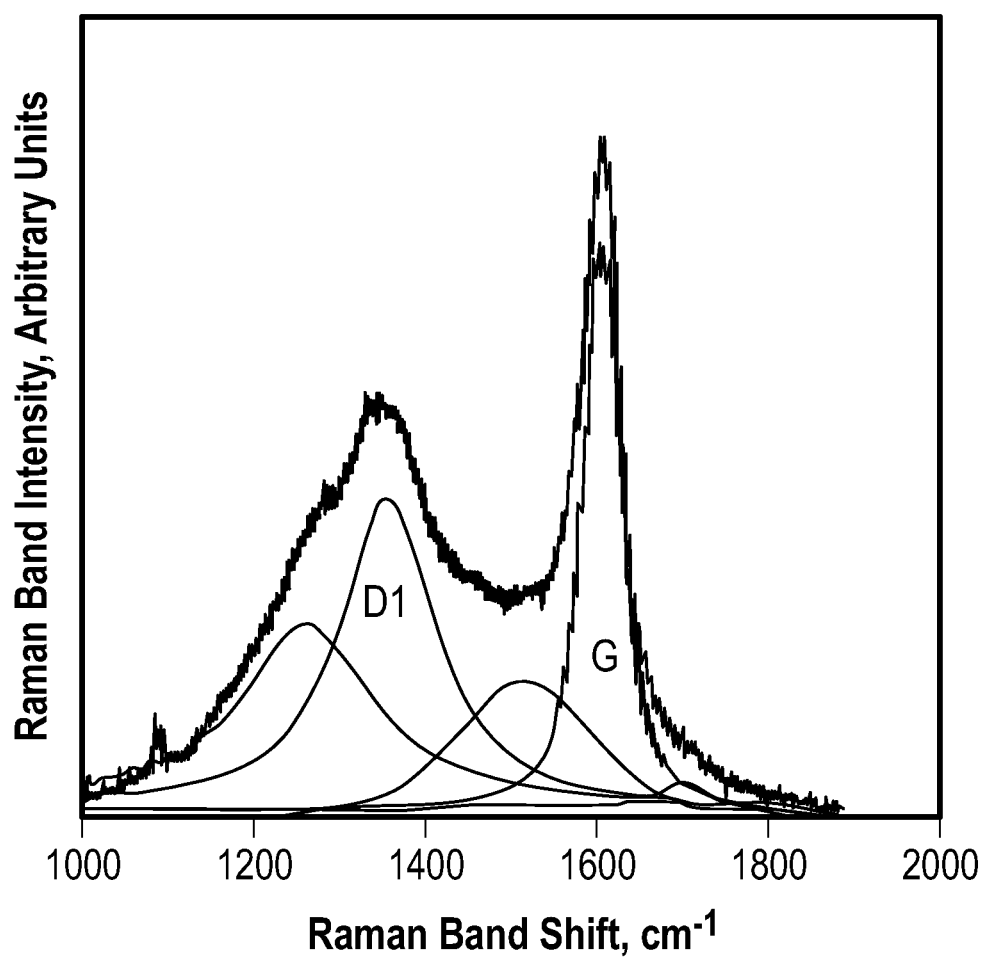
FIG. 7 depicts plots that illustrate quantification of Raman bands between 1000 $cm^{-1}$ and 1900 $cm^{-1}$.

In block 205, the Raman spectrum measured for each rock sample in block 203 is analyzed to determine data characterizing at least one Raman spectral feature for each rock sample. In embodiments, the at least one Raman spectral feature for each rock sample falls within a wavelength between at least ~1000 $cm^{-1}$ and 1877 $cm^{-1}$. In embodiments, the at least one spectral feature for each rock sample can correspond to one or more Raman bands or modes attributable to organic matter in the rock sample. For example, the at least one spectral feature for each rock sample can relate to one or more particular Raman bands in the rock sample selected from the group consisting of: Raman band positions, Raman band full-width at half-maxima (FWHM), Raman band areas, Raman band amplitudes, ratio of Raman band positions, ratio of Raman band FWHM, ratio of Raman band areas, and ratio of Raman band amplitudes. In embodiments, the at least one Raman spectral feature for each rock sample can be related to the 'G' (graphitic or ordered) band or peak and the 'D' (disordered) band or peak in the Raman spectrum of each rock sample, such as the mean 'G' band position and the mean 'D' band position, or the G/D ratio that quantifies the ratio of the intensities of the G and D band shifts according to the amplitudes or area of the band (FIG. 6). The 'G' band or peak indicates well-ordered, graphite-like carbon structures in kerogen within the rock sample and is due to the in-plane $E_{2g2}$ vibrational modes of the $sp^2$ carbon atoms in aromatic ring structures exhibiting $D_{6h}^4$ symmetry. The 'D' (disordered) band or peak results from Raman-active $A_{lg}$ symmetry and is connected to lattice defects and discontinuities of the $sp^2$ carbon network in kerogen within the rock sample. Examples of the 'G' band or peak and the 'D' band or peak is shown in FIG. 7 and discussed below. Additionally or alternatively, the at least one Raman spectral feature for each rock sample can be related to Raman band separation (RBS), which can be defined by the difference between mean 'G' band position and the mean 'D' band position or the difference between the position of the maximum 'G' band peak and the position of maximum 'D' band peak.

In embodiments, the data characterizing the Raman spectral features of the rock samples can be determined by background correction using one or more linear, polynomial, or other baseline fitting procedures to aid with the Raman spectral feature interpretation.

In block 207, correlation and regression analysis is performed on the data characterizing the Raman spectral features corresponding to the rock samples as determined in block 205 and the data quantifying the known or measured kerogen property (or asphaltene property) of the rock samples as collected in block 204 to determine a computational model that relates at least one Raman spectral feature of a rock sample to a value (or estimate) of such kerogen property (or asphaltene property) of the rock sample. In embodiments, the computational model can be a linear or non-linear mapping function that relates data characterizing at least one Raman spectral feature of a rock sample to a value of such kerogen property (or the asphaltene property) of the rock sample.

In embodiments, the correlation and regression analysis of block 207 can involve plotting the data characterizing the Raman spectral feature(s) of the rock samples as a function of the data quantifying the known or measured kerogen property (or asphaltene property) of the rock samples, and fitting a curve to the plotted points, e.g., using a best-fit regression.

Figure 3:
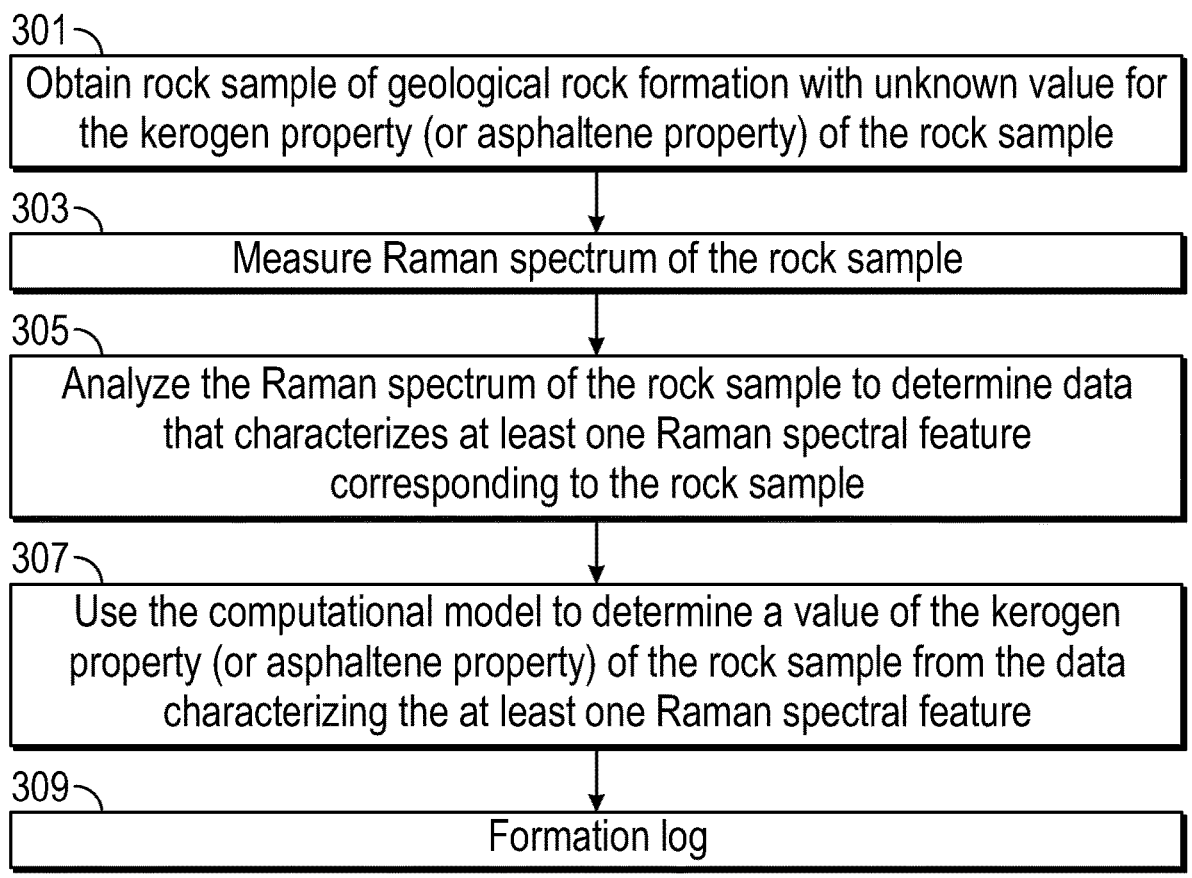
FIG. 3 is a flow diagram of a method that employs a Raman spectroscopy measurement on a rock sample of a geological rock formation with an unknown value of the kerogen property (or asphaltene property), analyzes the Raman spectral values obtained from the Raman spectroscopy measurement to determine data that characterize at least one Raman spectral feature of the rock sample, and supplies the data characterizing the at least one Raman spectral feature as input to the computation model which relates the data characterizing the Raman spectral feature(s) of the rock sample provided as input to a value (or estimate) of the kerogen property (or asphaltene property) of the rock sample.

FIG. 3 is a flow diagram of a method that employs a Raman spectroscopy measurement on a rock sample of a geological rock formation with an unknown value for the kerogen property (or the asphaltene property) of the rock sample together with the computation model of block 207 to determine a value (or estimate) of such kerogen property (or asphaltene property) of the rock sample.

The method begins in block 301 by obtaining a rock sample of a geological rock formation with an unknown value of the kerogen property (or the asphaltene property) of the rock sample. The rock sample can be a plug or sidewall core obtained from geological rock formation or part thereof (FIG. 4), a drill cutting obtained from a well drilling operation (FIG. 5), rock chips, crushed rock from drill cuttings or a core fragment, or other suitable rock sample.

In block 303, a Raman spectroscopy measurement is performed on the rock sample obtained in block 301 to acquire a Raman spectrum for the rock sample. In embodiments, the Raman spectroscopy measurement is performed by a Raman spectrometer. In embodiments, the Raman spectrum acquired by the Raman spectroscopy measurement includes spectral intensity values for wavelengths that cover the region of the IR spectrum between at least 1000 $cm^{-1}$ and 1877 $cm^{-1}$. In embodiments, the Raman spectrum for the rock sample can be acquired by multiple scans of the rock sample and averaging the measured Raman spectral response for the multiple scans.

In block 305, the Raman spectrum measured for the rock sample in block 303 is analyzed to determine data characterizing at least one Raman spectral feature for the rock sample. The determination of the at least one Raman spectral feature of the rock sample from the Raman spectrum can be similar to that described above in block 205 (which is used in generating the computational model of block 207).

In block 307, data characterizing the at least one Raman spectral feature of the rock sample as determined in block 305 is input to the computation model of block 207 which relates the data characterizing at least one Raman spectral feature of the rock sample provided as input to a value (or estimate) of the kerogen property (or asphaltene property) of the rock sample as output.

In block 309, the value (or estimate) of the kerogen property (or asphaltene property) of the rock sample as output from the computation model can be stored or output or displayed, for example, as part of a formation log. In this case, the value of the kerogen property (or asphaltene property) of the rock sample as output from the computational model in block 307 can be related to the known or measured depth of the rock sample obtained in block 301.

Note that one or more operations of the methodology of FIGS. 2 and/or 3 can be performed in the laboratory or possibly at a wellsite.

As described above, the computational model of block 207 can be configured to relate data characterizing at least one Raman spectral feature of a rock sample to a kerogen property (or asphaltene property) of the rock sample. In embodiments, the kerogen property (or asphaltene property) of the computational model can be particularly relevant to oilfield formation evaluation. One example of a kerogen property is kerogen density, which is a necessary input in the determination of density-porosity of kerogen-bearing geological rock formations, including petroleum source rocks. Another example of a kerogen property is kerogen Sigma (macroscopic cross-section for thermal neutron capture), which is a necessary input in the determination of Sigma-based saturation of kerogen-bearing geological rock formations. An example of an asphaltene property is asphaltene composition that can impact the viscosity and production of heavy oils in petroleum reservoirs.

Furthermore, the methods of FIGS. 2 and/or 3 can be repeated to generate and use a set of computational models where each computational model relates at least one Raman spectral feature of a rock sample to one of a plurality of different kerogen properties (or different asphaltene properties) of the rock sample, for example, as shown in FIGS. 8A-8D and described below in more detail.

The properties of organic matter in sedimentary rocks, including those explicitly disclosed herein that are related to kerogen and asphaltenes, are important in the exploration, evaluation, and development of hydrocarbon production from petroleum source rocks (shale) and petroleum reservoirs. Formation evaluation of organic-rich petroleum source rocks (commonly referred to as shale in the oilfield industry) requires an understanding of the amount and properties of sedimentary organic matter therein. Similarly, formation evaluation of conventional petroleum reservoirs can benefit from an understanding of the amount and properties of the organic matter in the reservoir, including petroleum and petroleum constituents such as bitumen and asphaltene. This subject disclosure describes a method for estimating properties of organic matter in a sample of a geological rock formation. The method uses Raman spectroscopy, available at the wellsite or in a laboratory, run on any formation sample such as drill core, drill cuttings, or outcrop, and correlates the Raman spectral signature obtained on the rock sample to a property of kerogen or asphaltenes in the rock sample.

For the purposes of the present disclosure, the organic matter exemplified is dispersed solid, insoluble, and non-volatile organic matter in petroleum source rocks, commonly termed kerogen. The methodology of the subject disclosure is equally applicable to characterizing other forms of organic matter in sedimentary rock amenable to study using Raman spectroscopy, such as asphaltenes or bitumen.

The methodology of the subject disclosure is useful for understanding properties of organic matter in any geological rock formation. Note that the geological rock formation may further comprise inorganic minerals as well. The organic matter may be in petroleum source rocks, including solid, insoluble, non-volatile organic matter, termed kerogen. The organic matter may be in petroleum reservoirs, including petroleum or constituents thereof, such as petroleum asphaltenes or bitumen.

Figure 4:
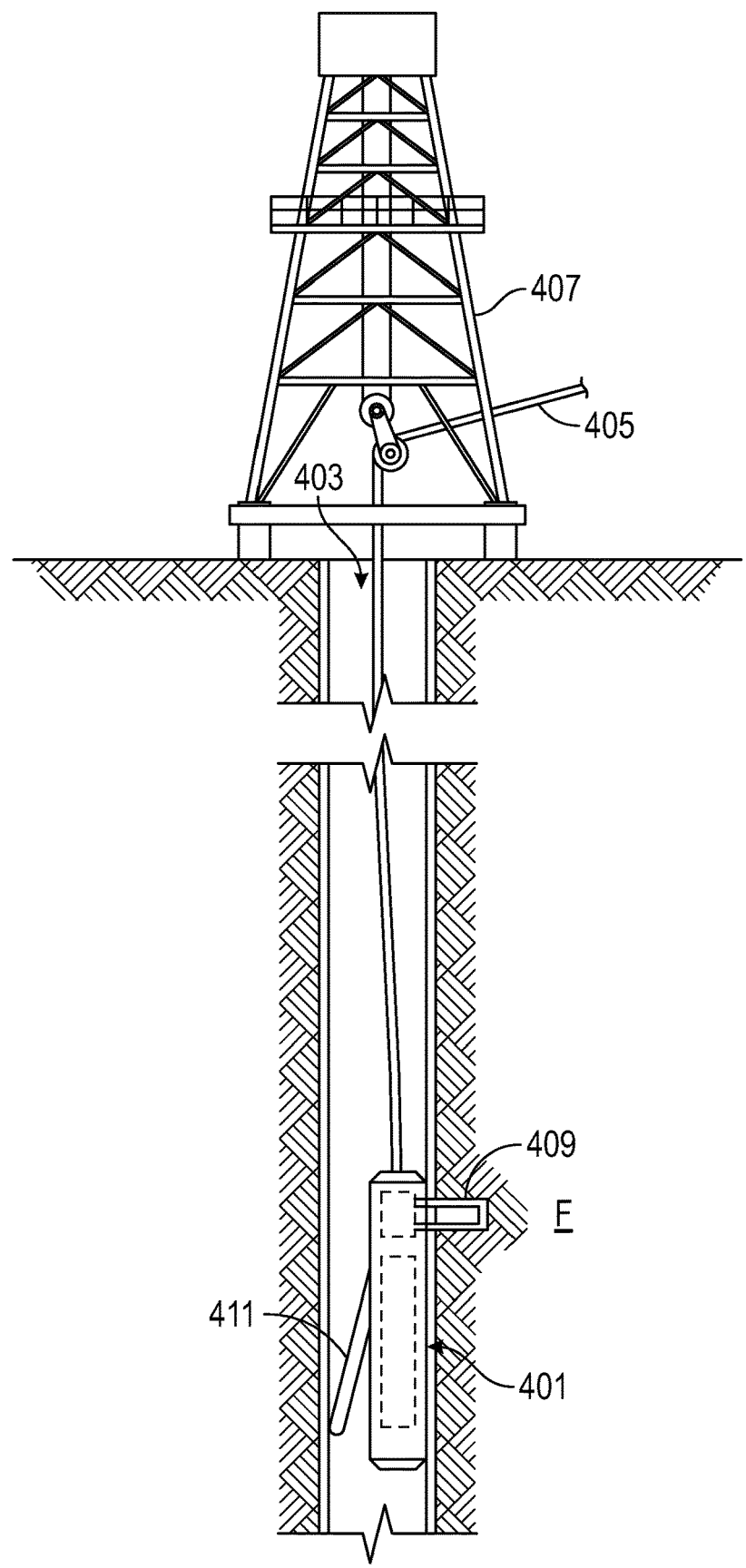
FIG. 4 is a diagram of a wellsite with equipment provided for acquiring a core rock sample of a geological rock formation.

FIG. 4 illustrates an example wellsite where a sidewall coring tool 401 is suspended in a borehole 403 by a wireline 405 supported by a rig 407. The borehole 403 traverses a geological rock formation F. A rock core sample of the geological rock formation may be taken using a coring bit 409 that is extended from the coring tool 401 into the formation F. The coring tool 401 may be braced in the borehole 403 by a support arm 411. An example of a commercially available coring tool of this type is the Mechanical Sidewall Coring Tool ("MSCT") by Schlumberger Corporation, the assignee of the present disclosure. The MSCT is further described in U.S. Pat. Nos. 4,714,119 and 5,667,025, both assigned to the assignee of the present disclosure.

FIG. 5 illustrates an example wellsite where a wellbore 501 is being drilled into a formation F. Equipment for drilling the formation F is located on the surface and extends into the wellbore 501 and typically includes a turn table, a kelly, drill pipe, a drill collar, a drill bit, a mud pump, shale shaker, etc. Also located on the surface is equipment 503 for collecting drill cuttings as the wellbore is being drilled. Specifically, one or more sieves can be used to separate drill cuttings from drilling mud. The drill cuttings can be cleaned and dried for analysis (FIG. 3). The cleaning can be designed in a way to effectively remove residues of drilling fluid (OBM or WBM) and any reservoir fluid from the drill cuttings.

FIG. 6 presents examples of Raman spectral features of rock samples of petroleum source rocks. For clarity, only the part of the Raman spectrum between 1000 $cm^{-1}$ and 1900 $cm^{-1}$ is shown.

FIG. 7 illustrates Raman spectral features of a rock sample from a petroleum source rock between 1000 $cm^{-1}$ and 1900 $cm^{-1}$ which is composed of partially resolved bands. It is known from previous studies that the principle Raman vibrational modes in this region of the spectrum of carbonaceous materials are associated with the energies of chemical bonds connected to $sp^2$ carbons in sheets of annulated aromatic carbon rings ('G' band, corresponding to 'graphitic' or 'ordered' carbon) and $sp^3$ carbons or bonds in an environment where the perfect graphene symmetry is broken by heteroatoms or aliphatic carbon moieties ('D' band, corresponding to 'disordered' carbon).

Organic matter property estimates are based on the observation that the characteristics of the Raman bands in the spectral region of interest (hereafter termed Raman spectral features) vary predictably and measurably with that property of interest. For example, the organic matter property estimate is based upon a determined relationship between one or more Raman spectral features and the organic matter property of interest. The region of the spectrum between ~ 1000 $cm^{-1}$ and 1877 $cm^{-1}$ is a part of the measurable spectrum amenable for characterization of organic matter.

It is common in Raman interpretations to solve for one or more Raman spectral feature parameters, such as: (1) "G/D ratio", quantifying the ratio of the intensities of the G and D band shifts as the band amplitudes or band areas; (2) "RBS" (Raman band separation), quantifying the separation between the centers (means) or maximum amplitudes of G and D band shifts.

FIGS. 8A-8D demonstrate by way of certain embodiments that Raman spectral features of organic matter are predictive of the properties of that organic matter. Here, the Raman spectral feature is expressed as the RBS, being the separation in Raman shift values between the G and D band centers (means) and the organic matter is kerogen.

Figure 8A:
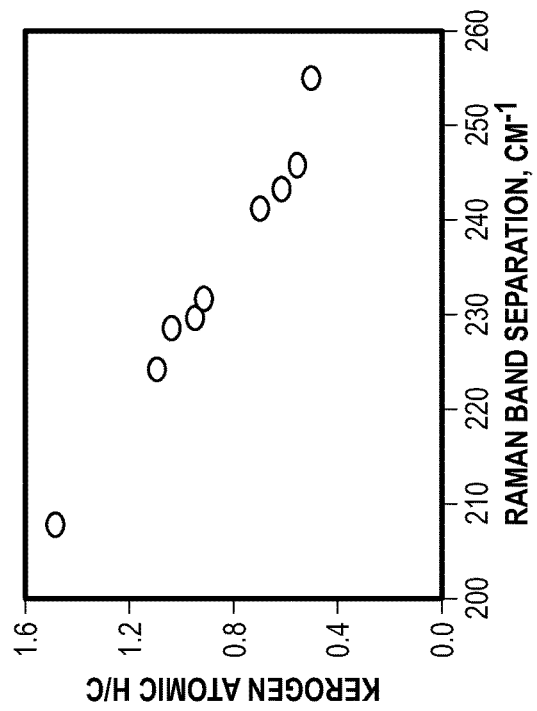
FIGS. 8A-8D depict plots of correlations between the Raman features of organic matter (Raman band separation, G band shift minus D band shift in wavenumbers, $cm^{-1}$) and certain properties of organic matter, which include kerogen density ($g/cm^3$) (FIG. 8A), kerogen atomic H/C ratio (FIG. 8B), kerogen specific surface area ($m^2/g$) (FIG. 8C), and kerogen thermal neutron porosity (p.u.) (FIG. 8D)
Figure 8B:
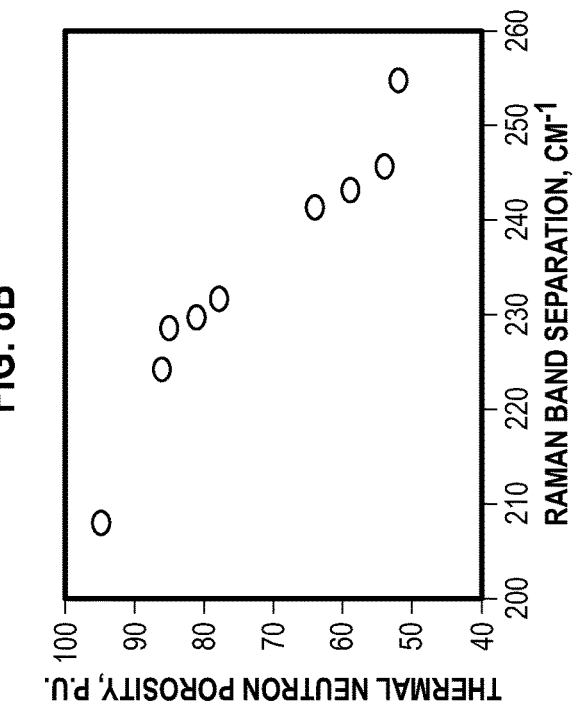
Figure 8C:
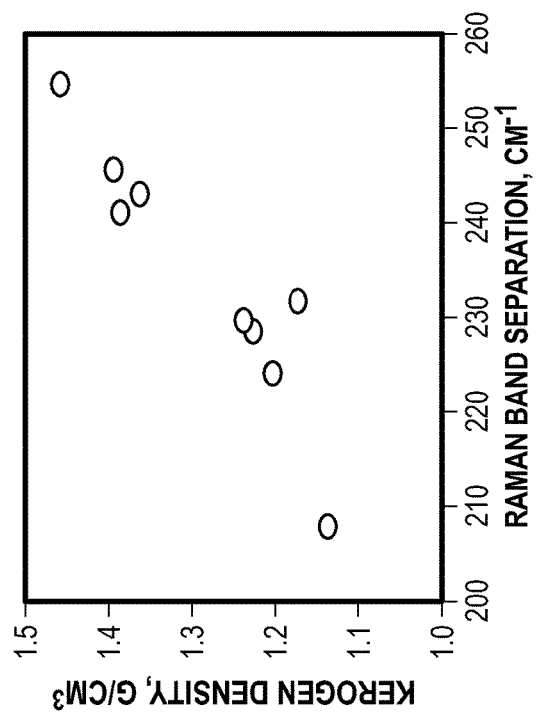
Figure 8D:
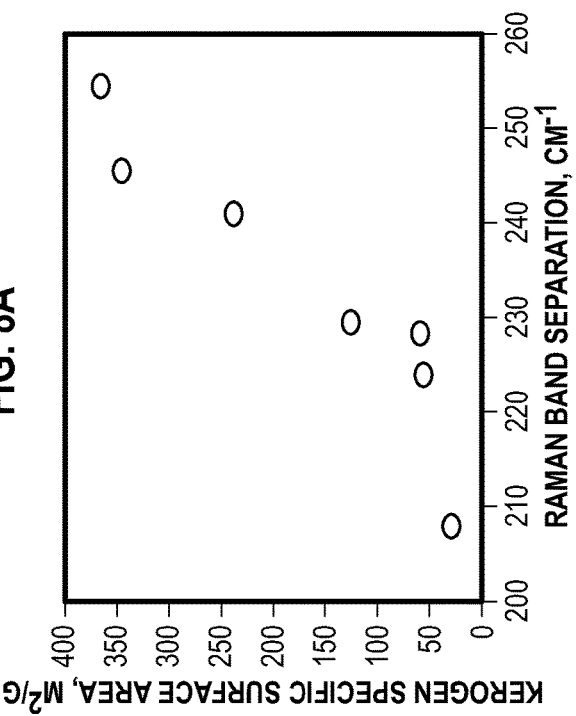

FIG. 8A shows the correlation between RBS of kerogen in a rock sample and the density of the kerogen. FIG. 8B shows the correlation between the RBS of kerogen in a rock sample and the atomic H/C ratio of the kerogen. FIG. 8C shows the correlation between the RBS of kerogen in a rock sample and the specific surface area of the kerogen. FIG. 8D shows the correlation between the RBS of kerogen in a rock sample and the neutron logging measurement response of the kerogen expressed as its thermal neutron porosity endpoint in porosity units. Analogous correlations exist between the RBS of kerogen in a rock sample and other kerogen properties, such as: its macroscopic capture cross-section for thermal neutrons (commonly termed Sigma); its dielectric permittivity; its electrical conductivity geochemical proxies for kerogen composition like pyrolysis $T_{max}$ and pyrolysis hydrogen index; or other properties not explicitly disclosed herein. Analogous correlations further exist between other Raman spectral features of kerogen, such as its G/D band ratio, and its properties.

Analogous correlations further exist between Raman spectral features and the properties of other organic matter phases not explicitly disclosed herein, such as petroleum asphaltenes or bitumen. The relationships embodied herein illustrate a means by which the values of the properties of organic matter in geological formation samples, in which the values are otherwise unknown, may be estimated by measuring the Raman spectral characteristics of organic matter in that sample.

Organic matter properties, including those explicitly disclosed herein are beneficial and necessary, for example, in the exploration, development, and production of petroleum resources from petroleum source rocks and petroleum reservoirs. By way of specific example, the kerogen density must be known to accurately compute porosity from a bulk density logging measurement using the well-known density-porosity relationship. The density-porosity method derives the porosity of a geological rock formation (the fractional volume of pore space between or within the solid rock in a geological formation) by 'correcting' the bulk density measurement for the matrix density of the rock of which kerogen may comprise a portion.

In an embodiment, a method by which a property of organic matter can be determined by a Raman measurement on formation samples is described. The method is beneficial because the Raman measurement may be performed on all types of geological formation samples with minimal sample preparation and sample destruction, avoiding the need to use alternative labor-intensive and destructive methods. Although we have described the general approach together with specific embodiments, it is inherently obvious to those skilled in the art that analogous transforms exist based on our Raman method that are not explicitly described herein.

Figure 9:
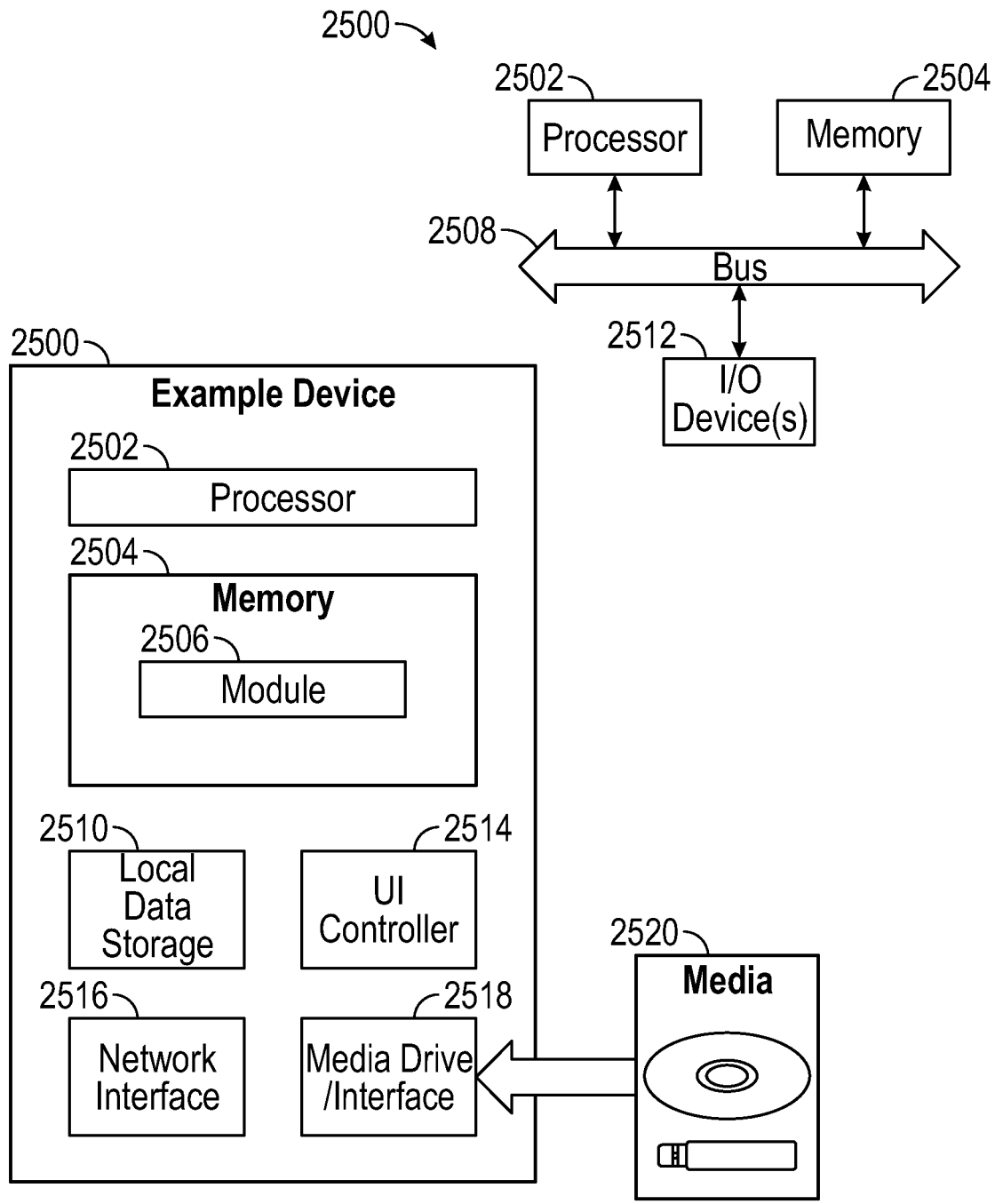
FIG. 9 is a block diagram of a computer processing system.

FIG. 9 illustrates an example device 2500, with a processor 2502 and memory 2504 that can be configured to implement various embodiments of the equipment, methods and workflows as discussed in this disclosure. Memory 2504 can also host one or more databases and can include one or more forms of volatile data storage media such as random-access memory (RAM), and/or one or more forms of non-volatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth). One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network. A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various systems and processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable, and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, general-purpose computer, special-purpose machine, virtual machine, software container, or appliance) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few example embodiments have been described in detail above, those skilled in the art will readily appreciate that many modifications are possible in the example embodiments without materially departing from this invention. For example, the methods and processes of the present disclosure can also be performed on organic matter isolated from the bulk formation sample in order to determine properties of the organic matter.

Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for characterizing organic matter in a geological rock formation, the method comprising:
   a) obtaining a rock sample of the geological rock formation;
   b) performing a Raman spectroscopy measurement on the rock sample to acquire a Raman spectrum of the rock sample; and
   c) using at least one processor to perform operations that involve
      i) analyzing the Raman spectrum of the rock sample to determine data characterizing at least one Raman spectral feature corresponding to the rock sample,
      ii) inputting the data characterizing the at least one Raman spectral feature corresponding to the rock sample into a computation model that determines a value of at least one property of organic matter in the rock sample given the data characterizing the at least one Raman spectral feature as an input, wherein the at least one property of organic matter includes a density of kerogen in the rock sample, and
      iii) storing or outputting or displaying the value of the property of organic matter in the rock sample.

2. The method of claim 1, wherein:
the property of organic matter in the rock sample includes at least one of atomic hydrogen-to-carbon (H/C) ratio of kerogen, specific surface area of kerogen, or thermal neutron porosity endpoint of kerogen.

3. The method of claim 2, wherein:
the property of organic matter in the rock sample includes at least one of macroscopic capture cross-section for thermal neutrons (Sigma) of kerogen, dielectric permittivity of kerogen, electrical conductivity of kerogen, a geochemical proxy for kerogen composition, pyrolysis $T_{max}$, or pyrolysis hydrogen index.

4. The method of claim 1, wherein:
the property of organic matter in the rock sample includes at least one of a property of asphaltenes or a property of bitumen in the rock sample.

5. The method of claim 1, wherein:
the Raman spectrum of the rock sample comprises spectral intensity for wavelengths that cover the region of the IR spectrum between at least 1000 $cm^{-1}$ and 1877 $cm^{-1}$.

6. The method of claim 1, wherein:
the Raman spectroscopy measurement of b) is performed by a Raman spectrometer.

7. The method of claim 1, wherein:
the at least one Raman spectral feature corresponds to one or more Raman bands or modes attributable to organic matter in the rock sample.

8. The method of claim 7, wherein:
the at least one spectral feature is related to particular Raman bands in the rock sample selected from the group consisting of: Raman band positions, Raman band full-width at half-maxima (FWHM), Raman band areas, Raman band amplitudes, ratio of Raman band positions, ratio of Raman band FWHM, ratio of Raman band areas, and ratio of Raman band amplitudes.

9. The method of claim 1, wherein:
the computation model is a linear or non-linear mapping function that relates the data characterizing the at least one Raman spectral feature of the rock sample to the value of the at least one property of organic matter in the rock sample.

10. The method of claim 1, wherein:
the rock sample is selected from the group consisting of core or plug, rock chips, drill cuttings, and rock outcrop.

11. The method of claim 1, wherein:
the operations of b) are carried out in a laboratory or at a wellsite.

12. The method of claim 1, wherein:
the operations of c) are carried out in a laboratory or at a wellsite.

13. The method of claim 1, further comprising:
repeating the operation of a), b) and c) for rock samples obtained from different depths of the formation to determine and output a log of an organic matter property of the formation as a function of depth in the formation.

14. The method of claim 1, further comprising:
generating the computation model of c) by determining data characterizing at least one Raman spectral feature for each one of a plurality of rock samples, and performing correlation and regression analysis on the data characterizing the Raman spectral features corresponding to the plurality of rock samples and data characterizing a known or measured organic property for each one of the plurality of rock samples.

15. The method of claim 14, wherein:
the data characterizing the at least one Raman spectral feature for each one of the plurality of rock samples is determined by measuring a Raman spectrum for each one of the plurality of rock samples and analyzing the Raman spectrum for each one of the plurality of rock samples.

16. A method for characterizing organic matter in a geological rock formation, the method comprising:
a) measuring a Raman spectrum for each one of a plurality of rock samples;
b) collecting data characterizing a known or measured organic property for each one of the plurality of rock samples, wherein the known or measured organic property includes a density of kerogen in the rock sample;
c) using at least one processor to perform operations that
  i) analyze the Raman spectrum for each one of the plurality of rock samples to determine data characterizing at least one Raman spectral feature for each one of the plurality of rock samples, and
  ii) perform correlation and regression analysis on the data characterizing the Raman spectral features corresponding to the plurality of rock samples and the data characterizing the known or measured organic property for each one of the plurality of rock samples to generate a computation model;
d) obtaining a particular rock sample of the geological rock formation;
e) performing a Raman spectroscopy measurement on the particular rock sample to acquire a Raman spectrum of the particular rock sample; and
f) using at least one processor to perform operations that involve
  i) analyzing the Raman spectrum of the particular rock sample to determine data characterizing at least one Raman spectral feature corresponding to the particular rock sample,
  ii) inputting the data characterizing the at least one Raman spectral feature corresponding to the particular rock sample into the computation model to determine a value of a density of kerogen in the particular rock sample given the data characterizing the at least one Raman spectral feature corresponding to the particular rock sample as an input, and
  iii) outputting or displaying the value of the density of kerogen in the particular rock sample.

17. The method of claim 16, wherein:
the property of organic matter in each one of the plurality of rock samples and in the particular rock sample includes at least one of: density of kerogen, atomic hydrogen-to-carbon (H/C) ratio of kerogen, specific surface area of kerogen, macroscopic capture cross-section for thermal neutrons (Sigma) of kerogen, thermal neutron porosity endpoint of kerogen, dielectric permittivity of kerogen, electrical conductivity of kerogen, geochemical proxy for kerogen composition, such as pyrolysis $T_{max}$, or pyrolysis hydrogen index.

18. The method of claim 16, wherein:
the known or measured organic property for each one of the plurality of rock samples includes at least one of a property of asphaltenes or a property of bitumen in each one of the plurality of rock samples; and
the property of organic matter in the particular rock sample as determined from the computational model includes at least one of a property of asphaltenes or a property of bitumen in the particular rock sample.

19. A method for characterizing organic matter in a geological rock formation, the method comprising:
a) obtaining a rock sample of the geological rock formation;
b) performing a Raman spectroscopy measurement on the rock sample to acquire a Raman spectrum of the rock sample; and
c) using at least one processor to perform operations that involve
  i) analyzing the Raman spectrum of the rock sample to determine data characterizing at least one Raman spectral feature corresponding to the rock sample,
  ii) inputting the data characterizing the at least one Raman spectral feature corresponding to the rock sample into a computation model that determines a respective value of each property of a plurality of properties of organic matter in the rock sample given the data characterizing the at least one Raman spectral feature as an input, wherein the plurality of properties of organic matter includes a density, an atomic hydrogen-to-carbon (H/C) ratio, a specific surface area, and a thermal neutron porosity endpoint of kerogen in the rock sample; and
  iii) storing or outputting or displaying the value of at least one property of the plurality of properties property of organic matter in the rock sample.

* * * * *